United States Patent
Burke

(10) Patent No.: US 10,980,856 B2
(45) Date of Patent: Apr. 20, 2021

(54) COMPOSITION AND METHOD FOR TREATING PLANTAR FASCIITIS IN HUMANS

(71) Applicant: Briant Burke, Boise, ID (US)

(72) Inventor: Briant Burke, Boise, ID (US)

( * ) Notice: Subject to any disclaimer, the term of this patent is extended or adjusted under 35 U.S.C. 154(b) by 441 days.

(21) Appl. No.: 16/169,599

(22) Filed: Oct. 24, 2018

(65) Prior Publication Data
US 2019/0183955 A1 Jun. 20, 2019

Related U.S. Application Data

(60) Provisional application No. 62/607,795, filed on Dec. 19, 2017.

(51) Int. Cl.
| | |
|---|---|
| A61K 36/61 | (2006.01) |
| A61K 47/10 | (2017.01) |
| A61K 47/20 | (2006.01) |
| A61P 19/04 | (2006.01) |
| A61K 9/00 | (2006.01) |
| A61P 29/00 | (2006.01) |
| A61K 47/22 | (2006.01) |

(52) U.S. Cl.
CPC ............ *A61K 36/61* (2013.01); *A61K 9/0014* (2013.01); *A61K 47/10* (2013.01); *A61K 47/20* (2013.01); *A61K 47/22* (2013.01); *A61P 19/04* (2018.01); *A61P 29/00* (2018.01)

(58) Field of Classification Search
CPC ........ A61K 36/61; A61K 47/10; A61K 47/20; A61K 47/22; A61K 9/0014; A61P 19/04; A61P 29/00
See application file for complete search history.

(56) References Cited

U.S. PATENT DOCUMENTS

| | | | |
|---|---|---|---|
| 9,095,607 B2 | 8/2015 | Cavallaro | |
| 9,669,099 B2 | 6/2017 | Cavallaro | |
| 10,010,572 B2* | 7/2018 | Parris | A61K 36/889 |
| 2008/0220103 A1* | 9/2008 | Birnbaum | A01N 65/28 |
| | | | 424/735 |

OTHER PUBLICATIONS

Smith, Douglas K and Gilley, James S., Imaging in sports injuries of the foot and ankle. Magn Reson Imaging Clin N Am 1999;7(1):131-149. 1999.
Hart, P.H., Brand, C. and Carson, C.F. (2000). Terpinen-4-ol, the main component of tea tree oil, suppresses inflammatory mediator production by activated human monocytes. Inflamm. Res., 49: 619-626. 2000.
Brand, C., Ferrante, A. and Prager, R.H. (2001). The water soluble components of the essential oil of M. altemifolia suppress the production of superoxide by human monocytes, but not neutrophils. Inflamm. Res., 50: 213-219. 2001.
Brand, C., Townley, S.I. and Finlay-Jones, J.J. (2002a). Tea tree oil reduces histamine-induced oedema in murine ears. Inflamm. Res., 51: 283-289. 2002.
Brand, C., Grimbaldston, M.A. and Gamble, J.R. (2002). Tea tree oil reduces the swelling associated with the efferent phase of a contact hypersensitivity response. Inflamm. Res., 51: 236-244. 2002.
Pearce, A., Finlay—Jones, J.J. and Hart, P.H (2005). Reduction of nickel-induced contact hypersensitivity reactions by topical tea tree oil in humans. Inflamm. Res., 54: 22-30. 2005.
Kanikkannan, N., et. al., "Structure-activity relationship of chemical penetration enhancers in transdermal drug delivery," Curr. Med. Chem., 7(6):593 (2000) 2000.
Parhi R, et. al., "Novel penetration enhancers for skin applications: a review," Curr. Drug Deliv., Mar. 2012;9(2):219-30 2012.
Wolgin M, Cook C, Graham C, Mauldin D. Conservative treatment of plantar heel pain: long-term follow-up. Foot Ankle Int 1994;15(3):97-102. 1994.
Ballas MT, Tytko J, Cookson D. Common overuse running injuries: diagnosis and management. Am Fam Physician 1997;55(7):2473-2484 1997.
Xuesheng, Han and Parker, Tory L., Anit-inflammatory activity of clove (*Eugenia caryophyllata*) essential oil in human dermal fibroblasts, Taylor & Francis, Pharmaceutical Biology 2017, vol. 55, No. 1, 1619-1622 2017.
Singh D, Angel J, Bentley G, Trevino SG. Fortnightly review. Plantar fasciitis. BMJ 1997;315(7101):172-175 (1997).
Riddle DL, Schappert SM. Volume of ambulatory care visits and patterns of care for patients diagnosed with plantar fasciitis: A national study of medical doctors. Foot Ankle Int 2004;25(5):303-310 (2004).
Irving DM, Cook JL, Young MA, Menz HB. Obesity and pronated foot type may increase the risk of chronic heel pain: a matched case-control study. BMC Musculoskelet Disord 2007;8:41(2007).
Buchbinder R. Clinical practice. Plantar fasciitis. N Engl J Med 2004;350(21):2159-2166 (2004).
Crawford F, Atkins D, Edwards J. Interventions for treating plantar heel pain. Cochrane Database Syst Rev 2000;(3): CD000416 (2000).
Riddle DL, Pulisic M, Pidcoe P, Johnson RE. Risk factors for plantar fasciitis: A matched case-control study. J Bone Joint Surg Am 2003;85(5):872-877 (2003).
Frey C, Zamora J. The effects of obesity on orthopaedic foot and ankle pathology. Foot Ankle Int 2007;28(9):996-999 (2007).

(Continued)

*Primary Examiner* — Aaron J Kosar
(74) *Attorney, Agent, or Firm* — Parsons Behle & Latimer

(57) ABSTRACT

A topical, non-prescription formulation of essential oils combined with skin permeation enhancers for the clinical treatment of plantar fasciitis in humans. The formulation may exclude black pepper essential oil. The present compositions and methods relate to a method for treating a disorder chosen from plantar fasciitis, bursitis, or arthritis in humans in a patient in need thereof, comprising administering to the patient compositions having a therapeutically effective amount of a combination of isoprenoidal essential oils, for example, Tea Tree Oil and Clove Bud Oil, in combination with a skin permeation enhancer, such as DMSO, the administration comprising contacting an affected area of skin of the patient with the composition.

23 Claims, 1 Drawing Sheet

(56) References Cited

OTHER PUBLICATIONS

Rano J, Fallat L, Savory-Moore R. Correlation of Heel Pain with Body Mass Index and Other Characteristics of Heel Pain, J. FOot and Ankle Surgery, 40(6), Dec. 2001, p. 351-356 (2001).
Rome K, Campbell R, Flint A, Haslock I. Heel pad thickness—a contributing factor associated with plantar heel pain in young adults. Foot Ankle Int 2002;23(2):142-147 (2002).
Kibler WB, Goldberg C, Chandler TJ. Functional biomechanical deficits in running athletes with plantar fasciitis. Am J Sports Med 1991;19(1):66-71 (1991).
Narvaez JA, Narvaez J, Ortega R, et al. Painful heel: MR imaging findings. Radiographics 2000;20(2):333-352 (2000).
Furey JG. Plantar fasciitis. The painful heel syndrome. J Bone Joint Surg Am 1975;57(5):672-673 (1975).
Matheson GO, Macintyre JG, Taunton JE, et al. Musculoskeletal injuries associated with physical activity in older adults. Med Sci Sports Exerc 1989;21(4):379-385 (1989).
Taunton JE, Ryan MB, Clement DB, et al. A retrospective case-control analysis of 2002 running injuries. Br J Sports Med 2002;36(2):95-101 (2002).
Rome K, Howe T, Haslock I. Risk factors associated with teh development of planter heel pain in athletes, The Foot, 11, pp. 119-125 (2001).
Wearing SC, Smeathers JE, Yates B, et al. Sagittal movement of the medial longitudinal arch is unchanged in plantar fasciitis. Med Sci Sports Exerc 2004;36(10):1761-1767 (2004).
Prichasuk S, Mulpruek P, Siriwongpairat P. The heel-pad compressibility. Clin Orthop Relat Res 1994;(300):197-200 (1994).
Lapidus PW, Guidotti FP. Painful heel: Report of 323 Patients with 364 painful heels. Clin Orthop Relat Res 1965;39:178-186 (1965).
Scott G, Menz HB, Newcombe L. Age-related differences in foot structure and function. Gait Posture 2007;26(1):68-75 (2007).
Redmond AC, Crosbie J, Ouvrier RA. Development and validation of a novel rating system for scoring standing foot posture: the Foot Posture Index. Clin Biomech 2006;21(1):89-98 (2006).
Sadat-Ali M. Plantar fasciitis/calcaneal spur among security forces personnel. Mil Med 1998;163(1):56-57 (1998).
Pfeffer G, Bacchetti P, Deland J, et al. Comparison of custom and prefabricated orthoses in the initial treatment of proximal plantar fasciitis. Foot Ankle Int 1999;20(4):214-221 (1999).
Scher DL, Belmont PJ Jr, Bear R, et al. The incidence of plantar fasciitis in the United States military. J Bone Joint Surg Am 2009;91(12):2867-2872 (2009).
Beeson, P. Foot Ankle Surg. Sep. 2014;20(3):160-5 Plantar fasciopathy: revisiting the risk factors (2014).
Cutts S, Obi N, Pasapula C, Chan W (2012). "Plantar fasciitis". Ann R Coll Surg Engl. 94 (8): 539-42 (2012).
Caldefie-chezet, F., Guerry, M. and Chalchat, J.C. (2004). Anti-inflammatory effects of M. alternifolia essential oil on human polymorphonuclear neutrophils and monocytes. Free Rad. Res., 38: 805-811 (2004).
Khalil, Z.A., Pearce, A.L. and Satkunanathan, N. (2004). Regulation of wheal and flare by tea tree oil. J. Investig. Dermatol., 123: 683-690 (2004).
Koh, K.J., Pearce, A.I. and Marshaman, G. (2002). Tea tree oil reduces histamine-induced skin inflammation. Br. J. Dermatol., 147: 1212-1217 (2002).
Pazyar, N. and Yaghoobi, R. (2012) Tea tree oil as a novel antipsoriasis weapon.Skin Pharmacol. Physiol., 25: 162-163 (2012).
Grespan R, et. al 2012 Anti-arthritic effect of eugenol from Clove Bud Oil on collagen-induced arthritis experimental model. Biol Pharm Bull 35(10): 1818-1820 (2012).
Han, X., and Parker, T.L., "Anti-inflammatory Activity of Clove (*Eugenia caryophyllata*) Essential Oil in Human Dermal Fibroblasts," Pharm. Biol., Dec. 2017;55(1):1619-1622. doi: 10.1080/13880209.2017.1314513 (2017).
Sinha, V.R., et. al., "Permeation Enhancers for Transdermal Drug Delivery," Drug Dev. Ind. Pharm., 26(11):1131 (2000).
Chen J., et. al., "Natural Terpenes as Penetration Enhancers for Transdermal Drug Delivery," Molecules, Dec. 11, 2016;21(12), pii: E1709, (2016).
Lemont H, Ammirati KM, Usen N. Plantar fasciitis. A degenerative process (fasciosis) without inflammation. J Am Podiatr Med Assoc 2003;93(3):234-237 (2003).

\* cited by examiner

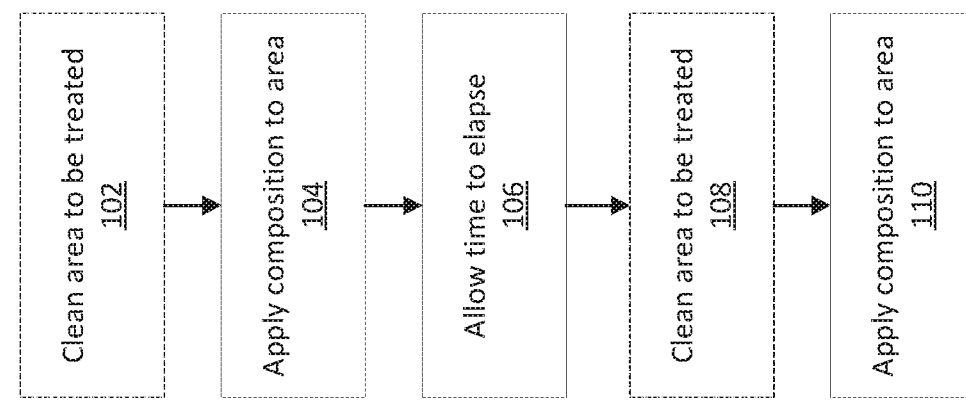

COMPOSITION AND METHOD FOR TREATING PLANTAR FASCIITIS IN HUMANS

CROSS-REFERENCE TO RELATED APPLICATIONS

This application, under 35 U.S.C. § 119, claims priority to and the benefit of U.S. Provisional Patent Application Ser. No. 62/607,795 filed on Dec. 19, 2017, and entitled "Composition and Method for Treating Plantar Fasciitis in Humans," the contents of which are hereby incorporated by reference herein.

FIELD OF THE DISCLOSURE

The present compositions and methods of treatment relate generally to anti-inflammatory compositions, and more specifically, to anti-inflammatory compositions derived from essential oil of *Melaleuca alternifolia* and clove bud oil when combined with a skin permeation enhancer for the clinical treatment of plantar fasciitis and to relieve inflammation at the site. The compositions and methods may exclude black pepper essential oil.

BACKGROUND

Plantar fasciitis is the most common cause of heel pain presenting to the outpatient clinic, and 10% of the population may present with heel pain over the course of their lives. Between 4% and 7% of people have heel pain at any given time and about 80% of these cases are due to plantar fasciitis. Plantar fasciitis is diagnosed on the basis of a history of pain on taking the first few steps in the morning, worsening pain with weight-bearing, and pain and tenderness to palpation over the medial calcaneal tubercle. Patients may have decreased ankle dorsiflexion secondary to a tight Achilles tendon. Up to one third of patients with plantar fasciitis will present with bilateral symptoms.

Etiology

Plantar fasciitis is multifactorial in etiology. Intrinsic factors include age, excessive foot pronation, obesity and limited ankle dorsiflexion. Extrinsic factors include occupational prolonged weight-bearing, inappropriate shoe wear, and rapid increases in activity level. These factors combine to create a pathologic overload of the plantar fascia at the calcaneal insertion, causing microtears in the fascia that subsequently lead to perifascial edema and increasing heel pad thickness.

As microtears within the fascia increase in size and become symptomatic, inflexibility of the posterior structures of the foot, combined with weakness of the plantar flexors during the pushoff phase of the gait cycle, alters the normal biomechanics of the foot, creating an environment of decreased efficiency of force absorption and production. The decrease in force absorption contributes to the overload of the plantar fascia and increasing degenerative changes, which include collagen necrosis, angiofibroblastic hyperplasia, chondroid metaplasia and matrix calcification. Plantar fasciitis can also be associated with various forms of arthritis, but in approximately 85% of cases there are no known systemic factors.

In runners, plantar fasciitis is primarily believed to be an overuse injury combined with training errors, training surfaces, biomechanical alignment and muscle dysfunction and inflexibility. For example, excessive pronation of the foot leads to increased tension on the plantar fascia during the stance phase of running. In athletes who are just beginning their training programs, the lower limb muscles may have yet to develop the necessary strength and flexibility, and shock absorption can be negatively affected.

Epidemiology

Ten percent of people in the United States may present with heel pain over the course of their lives, with 83% of these patients being active working adults between the ages of 25 and 65 years old. A recent survey of members of the American Podiatric Medical Association revealed that plantar fasciitis/heel pain was the most prevalent condition being treated in podiatric clinics. Within the current literature, prevalence rates of plantar fasciitis among a population of runners have been shown to be as high as 22%

The association of plantar fasciitis with increasing age is consistent with the histopathological findings of degenerative and inflammatory changes within the plantar fascia. These findings support the hypothesis that plantar fasciitis is secondary to repetitive microtrauma caused by prolonged weight-bearing activities. The constant overload inhibits the normal repair process, resulting in collagen degeneration, which causes both structural changes and perifascial edema. These changes in turn lead to a thicker heel pad, which has been shown to be associated with pain in individuals with plantar fasciitis.

Increasing heel pad thickness leads to a loss of heel pad elasticity; both of these factors are associated with increasing age and increasing body mass index (BMI). The decrease in elasticity of the fascia seen with increasing age is associated with a decrease in shock absorbing capabilities, which may be a result of the degenerative fascia's inability to resist normal tensile loads. It is this decrease in shock absorbing capability that is believed to cause the pain associated with plantar fasciitis.

In order to determine epidemiological risk factors and the current incidence of plantar fasciitis within a population of individuals with a high level of physical activity, one study (see, Scher, D. L., Belmont, P. J. Jr, Bear, R, et al., "*The Incidence of Plantar Fasciitis in the United States Military*," J. Bone Joint Surg. Am., 2009; 91(12):2867-2872, which is incorporated in its entirety herein by reference) accessed a database from the United States Armed Forces. The United States Armed Forces represent a physically active population of ethnically diverse male and female service members with generally high occupational demands. In this comprehensive study, female subjects, when compared with male subjects, were twice as likely to develop plantar fasciitis as their male counterparts. These findings are based on incidence rates, but tend to correlate with prevalence data seen within the existing literature. The overall incidence of plantar fasciitis in the military population was 10.55 per 1,000 person-years. Members of the Army and Marines were more likely to get plantar fasciitis than those in the Air Force.

Increased body weight and increased BMI have been shown to be significant risk factors for plantar fasciitis. Subjects with a BMI of more than 30 being over 5.6 times as likely to get plantar fasciitis compared to someone with a BMI less than 25.

Another study, (see, Riddle, D. L., Pulisic. M., Pidcoe, P., and Johnson, R. E., "*Risk Factors for Plantar Fasciitis: A Matched Case-Control Study*," J. Bone Joint Surg. Am., 2003; 85(5):872-877, which is incorporated in its entirety herein by reference) hypothesized that reduced ankle dorsiflexion is the most important risk factor for the development of plantar fasciitis, as the greater the limitation in ankle dorsiflexion, the greater the amount of compensatory foot pronation and therefore the higher level of loading on the plantar fascia.

Another study (see, Scott, G., Menz, H. B., and Newcombe, L., "*Age-Related Differences in Foot Structure and Function,*" Gait Posture, 2007; 26(1):68-75, which is incorporated in its entirety herein by reference) found that older patients (mean age 80.2) had reduced ankle range of motion compared with younger patients (mean age 20.9). Other studies have shown an exponential relationship between decreasing ankle dorsiflexion and the risk of developing plantar fasciitis has been found, with individuals who have 0° of dorsiflexion or less having an odds ratio of 23.3 (95% confidence interval, 4.3 to 124.4). Foot pronation alone, for example, as measured by the Foot Posture Index (see, Redmond, A. C., Crosbie, J., and Ouvrier, R. A., "*Development and Validation of a Novel Rating System for Scoring Standing Foot Posture: the Foot Posture Index,*" Clin. Biomech., 2006; 21(1):89-98, which is incorporated in its entirety herein by reference) has also been shown to be significantly greater in patients with chronic plantar heel pain.

In addition to these intrinsic factors, various extrinsic factors have been related to the development of plantar fasciitis. Several studies have shown an association between work-related prolonged weight-bearing and plantar fasciitis. For example, in some case series (see, e.g., Lapidus, P. W. and Guidotti, F. P., "*Painful Heel: Report of* 323 *Patients with* 364 *Painful Heels,*" Clin. Orthop. Relat. Res., 1965; 39:178-186, which is incorporated in its entirety herein by reference) patient population included a predominance of occupations that necessitate continual standing or walking, such as waiters, maids, and kitchen workers. In addition, each heel strike during running causes compression of the heel pad up to 200% of body weight.

Therefore, in individuals who may not have adequate muscle strength or flexibility, and therefore have decreased shock-absorbing capabilities, the initiation of a new training program can exacerbate overloading of the plantar fascia. Increases in tensile loading, seen with new increases in running intensity or frequency and changes in general footwear have been associated with overloads of the plantar fascia leading to microtears.

Other drawbacks and issues with existing treatments for planar fasciitis also exist.

SUMMARY

10% of the population may present with heel pain over the course of their lives. Obesity, decreased ankle dorsiflexion, a pronated foot, and increasing age are among the important intrinsic risk factors that have been associated with plantar fasciitis. The extrinsic risk factors include, but are not limited to, prolonged occupational weightbearing, increasing activity levels, and inappropriate shoe wear.

Accordingly, there are herein disclosed methods and compositions for use in treating plantar faciitis in human subjects.

Disclosed embodiments include a composition made of essential oil of tea tree oil (*Melaleuca alternifolia*), essential oil of clove bud oil (*Syzygium aromaticum*), a skin permeation agent, and an alcohol carrier, or an inert carrier oil. Embodiments of the composition use a skin permeation agent such as DMSO (dimethylsulphacetamide or dimethylsulfoxide), terpenes, long chain alcohols, pyrrolidones, and cinnamene compounds. Embodiments of the composition use an alcohol carrier or inert carrier oil such as 1-propanol, isopropyl alcohol (2-propanol), ethanol, methanol, benzyl alcohol, cetyl alcohol, butanol, pentanol, hexanol, cyclohexanol, isobutyl alcohol, tert-amyl alcohol, almond oil, and canola oil.

Embodiments of the composition may use tea tree oil in a concentration ranging from 1% (v/v) to 50% (v/v), the essential oil of clove bud oil is present at a concentration ranging from 1% (v/v) to 50% (v/v), the suitable carrier alcohol or inert carrier oil is present at a concentration from 10% (v/v) to 80%, (v/v) and the skin permeation agent is present in concentration from 1% (v/v)-25% (v/v).

Other disclosed embodiments of the composition use tea tree oil in a concentration ranging from 7% (v/v) to 20% (v/v), the essential oil of clove bud oil is present at a concentration ranging from 1% (v/v) to 5% (v/v), the suitable carrier alcohol or inert carrier oil is present at a concentration from 60% (v/v) to 80%, (v/v) and the skin permeation agent is present in concentration from 5% (v/v)-20% (v/v).

Other disclosed embodiments of the composition use a skin permeation agent of DMSO and the concentration of tea tree oil is 15%, the concentration of essential oil of clove bud oil is 3%, the concentration of the DMSO is 13%, and the concentration of the alcohol carrier or inert carrier oil is 69%.

Other disclosed embodiments of the composition use a skin permeation agent such as DMSO, terpenes, limonene, a mixture of terpenes, long chain alcohols, 1-octanol, and members of the pyrrolidone class of organic compounds.

Also disclosed are methods of treating an inflammatory condition in a human subject, the method including administering to the skin of the human subject in the area of the inflammatory condition a compound made of essential oil of tea tree oil, essential oil of clove bud oil, a skin permeation agent, and an alcohol carrier, or an inert carrier oil.

Also disclosed are methods of making a compound usable for treatment of an inflammatory condition in human subjects, the method including mixing a compound made of essential oil of tea tree oil, essential oil of clove bud oil, a skin permeation agent, and an alcohol carrier, or an inert carrier oil.

While tea tree oil and clove oil are both known to possess anti-inflammatory activity, the pronounced synergistic effect seen with disclosed combination is unexpected, surprising, novel, and not something that a person skilled in the art would have been able to predict. Other advantages, efficiencies, and benefits of disclosed embodiments also exist.

BRIEF DESCRIPTION OF THE DRAWINGS

FIG. 1 is an exemplary flow chart of embodiments of treating plantar fasciitis in accordance with the disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

Disclosed embodiments include one or more of the following essential oils.

Melaleuca alternifolia (TTO)

As used herein, the term "tea tree oil" or "TTO" means (1) the actual essential oil of the species Melaleuca alternifolia conforming to Standards Association of Australia (SAA) AS 2782-1985, and/or (2) the active component or components derived from said tea tree oil.

TTO has been reported to have anti-inflammatory properties demonstrating that TTO affects a host of immune responses both in vitro and in vivo. For example, Hart, P. H., Brand, C. and Carson, C. F., "Terpinen-4-ol, The Main Component of Tea Tree Oil, Suppresses Inflammatory Mediator Production by Activated Human Monocytes," Inflamm. Res., (2000) 49: 619-626, which is incorporated in its entirety herein by reference, demonstrated that terpinen-4-ol (the largest component of TTO comprising up to 43% by volume of the whole oil) inhibited the lipopolysaccharide-induced product of inflammatory mediators TNF-α, interleukin-1b (IL-1b), and IL-10 by human peripheral blood monocytes by 50% and prostaglandin E2 by 30% after 40 hours.

The water soluble fraction of TTO, terpinen-4-ol, and a-terpineol have been shown to suppress superoxide production by agonist-stimulated monocytes, but not neutrophils. Similar studies have shown TTO decreases the production of reactive oxygen species by both neutrophils and monocytes.

In vivo, topically applied TTO has been shown to reduce edema associated with the efferent phase of contact hypersensitivity reaction in mice, an effect attributed to the terpinen-4-ol and á-terpineol components of the oil. The mice were sensitized to a chemical hapten on their ventral skin and seven days later challenged with the same hapten on their dorsal skin. TTO applied 30 minutes before and up to 7 hours after to the same dorsal site as hapten challenge caused a significant reduction in skin swelling at 24 hours. TTO reduced edema but did not affect the influx of inflammatory cells, and TTO did not suppress UVB-induced edema. See, e.g., Brand, C., Grimbaldston, M. A. and Gamble, J. R., "Tea tree oil reduces the swelling associated with the efferent phase of a contact hypersensitivity response," Inflamm. Res., 51: 236-244 (2002) which is incorporated in its entirety herein by reference.

In another study where Balb/c mice injected with histamine to induce a Type I allergic immediate hypersensitivity reaction, TTO and terpinen-4-ol applied immediately after histamine injection, but not before, reduced histamine-induced skin edema. This effect was the same in capsaicin treated and control mice which suggests that TTO did not inhibit the histamine induced edema by regulating the activity of peripheral sensory neurons. See, e.g., Brand, C., Townley, S. I. and Finlay-Jones, J. J., "Tea tree oil reduces histamine-induced oedema in murine ears," Inflamm. Res., 51: 283-289 (2002a) which is incorporated in its entirety herein by reference.

Human studies on the histamine-induced wheal and flare response further support the animal and in vitro data. For example, when twenty-seven volunteers were injected intradermally with histamine, flare and wheal diameters and double skin thickness were measured every 10 minutes for 1 hour to calculate flare and wheal volume. At 20 minutes, 25 microliters of 100% TTO was applied topically to the study volunteers. Controls received paraffin oil. TTO significantly reduced mean wheal flare volume (P=0.0004) but not flare area. See, e.g., Khalil, Z. A., Pearce, A. L. and Satkunanathan, N., "Regulation of wheal and flare by tea tree oil," J. Investig. Dermatol., 123: 683-690 (2004) and Koh, K. J., Pearce, A. I. and Marshaman, G., "Tea tree oil reduces histamine-induced skin inflammation," Br. J. Dermatol., 147: 1212-1217 (2002) which are incorporated in their entirety herein by reference.

The effect of TTO on nickel-induced contact hypersensitivity reactions in human dorsal skin has also been examined. For example, TTO at 100%, but not 5% or 100% macadamia oil, reduced the flare area and erythema index when applied at days 3 and 5 after nickel exposure. In addition, terpinen-4-ol has shown potential as a novel agent in treating psoriasis.

Clove Bud Oil

As used herein, clove bud oil means (1) the actual essential oil of the species eugenia caryophyllata or syzygium aromaticum, and/or (2) the active component or components derived from said clove bud oil. Some studies have found the anti-inflammatory activity of clove (eugenia caryophyllata) essential oil in human dermal fibroblasts. See, for example, Han, X., and Parker, T. L., "Anti-inflammatory Activity of Clove (Eugenia caryophyllata) Essential Oil in Human Dermal Fibroblasts," Pharm. Biol., 2017 December; 55(1):1619-1622. doi: 10.1080/13880209.2017.1314513; and Grespan, R., et. Al., "Anti-arthritic Effect of Eugenol from Clove Bud Oil on Collagen Induced Arthritis Experimental Model," Biol. Pharm. Bull., 2012:35(10): 1818-1820, which are incorporated in their entirety by reference herein.

Transdermal Delivery

Some disclosed embodiments include topical solutions that may be applied to the skin for transdermal delivery of the treatment. It will be appreciated by persons skilled in the art of topical drug delivery, or transdermal drug delivery, having the benefit of this disclosure that a variety of skin permeation enhancers may be selected for use with the disclosed embodiments as is known in the art. A review of enhancers is provided, for example, Sinha, V R., et. al., "Permeation Enhancers for Transdermal Drug Delivery," Drug Dev. Ind. Pharm., 26(11):1131 (2000), or Kanikkannan, N., et. al., "Structure-activity relationship of chemical penetration enhancers in transdermal drug delivery," Curr. Med. Chem., 7(6):593 (2000), or more recently, Chen J., et. al., "Natural Terpenes as Penetration Enhancers for Transdermal Drug Delivery," Molecules, 2016 Dec. 11; 21(12), pii: E1709, (2016), or Parhi R, et. al., "Novel penetration enhancers for skin applications: a review," Curr. Drug Deliv., 2012 March; 9(2):219-30, which are hereby incorporated by reference. For example, skin permeation enhancers such as, dimethylsulphacetamide or dimethylsulfoxide, terpenes, long chain alcohols, pyrrolidones, and other enhancers as described in the above-noted articles may be used in embodiments as disclosed below.

Benefits in transdermal uptake of the essential oils can be obtained by formulating the oils with a skin permeation enhancer, including but not limited to the following.

1) DMSO. Suitable skin permeation enhancing agents include dimethylsulphacetamide or dimethylsulfoxide (DMSO). DMSO is known for its effectiveness as a skin permeation enhancer, as well as its excellent solvent properties for both water soluble and insoluble substances.

2) Terpenes: e.g., limonene.

3) Long chain alcohols, e.g., 1-octanol.

4) Pyrrolidones, e.g., doxapram, piracetam.

5) cinnamene compounds, e.g., cinnamic acid, cinnamaldehyde.

Suitable preparations for topical application include, but are not limited to, liquid preparations, with or without viscosity enhancing agents, where the tea tree oil and clove oil are combined with a pharmaceutically acceptable carrier, emulsions, both water-in-oil and oil-in-water, ointments, creams, lotions, gels, sprays, salves, sticks, soaps or any other appropriate preparation. Such topical pharmaceutical compositions are formulated by conventional methods well known in the art. Topical patches or bandages containing the tea tree oil and clove oil are also suitable for use. The composition can include any number of additional components such as preservatives, perfumes, colorants, and skin penetration enhancers. The precise concentrations of components in the topical compositions of the invention will depend of course on a number of factors including, for example, the severity of the condition to be treated, and the physical nature of the pharmaceutical composition.

Alcohol Carriers

Embodiments of the composition may also include a suitable alcohol carrier or include a suitable inert carrier oil, such as almond oil or canola oil. Concentrated essential oils applied directly to the skin may cause irritation, necessitating dilution. Essential oils are not miscible with water, but are with alcohols, which thus can provide a convenient and well tolerated excipient. For example, alcohol carriers such as 1-propanol, isopropyl alcohol (2-propanol), ethanol, methanol, benzyl alcohol, cetyl alcohol, butanol, pentanol, hexanol, cyclohexanol, isobutyl alcohol, and tert-amyl alcohol may be used.

Clinical Data

Studies were performed in support of disclosed treatment methods as described below. Patients with physician-diagnosed plantar fasciitis were randomized into a placebo controlled blinded trial on a rolling basis in an on-going clinical trial comparing the effect of a mixture of A) 100% tea tree oil, 100% clove oil, and DMSO as the permeation enhancer, B) 100% tea tree oil+DMSO, and C) 100% clove bud oil+DMSO. Composition A contained 3% clove bud oil/13% DMSO/15% tea tree oil/69% isopropyl alcohol. Composition B contained 15% tea tree oil/13% DMSO/72% isopropyl alcohol. Composition C contained 3% clove bud oil/13% DMSO/84% isopropyl alcohol. Patients were recruited from the offices of a primary care physician, a podiatrist, and a physical therapy group practice. Informed consent was obtained and all protocols were in compliance with the International Standards for Clinical Research (ICH GCP 4.1.3).

Fifty one (51) patients, 23 male and 28 female, completed the protocol, and study results for this cohort of patients are presented below in Table 1. There was no statistical age difference between the groups. Average duration of symptoms was 4±4 months and was not statistically different between groups.

Upon enrollment, patients were asked to rate their pain over the previous 7 days using a numerical analog scale ranging from 0-10, with 0 representing no pain and 10 being excruciating pain.

Patients were instructed to wash the bottom of the affected foot with soap and water prior to application, pat dry, then apply treatment to the bottom of the heel of the foot using the applicator brush attached to the bottle cap. They were to do this twice a day. Patients were seen in follow up 1 week later from the date they began application. Analysis is for participants completing the study. Four patients were enrolled but were lost to follow up and are not included in analysis. At the follow up visit the participants were asked to again rate their pain using the same numerical scale. Statistical analysis was by 1-Way ANOVA.

TABLE 1

| Clinical Data | | | |
|---|---|---|---|
| | Composition A (TTO) | Composition B (Clove) | Composition C (TTO + Clove) |
| Mean Pain Score Day 0 | 6.8 ± 1.7^ | 6.1 ± 1.6^ | 6.6 ± 1.4^ |
| Mean Pain Score Day 7 | 5.4 ± 1.3^ | 5.6 ± 1.7^ | 1.1 ± 0.9* |

^P = 0.46. There were no differences between these group mean scores.
*P < 0.001 Compared to control.

Twice daily application of the Composition C formulation of 3% clove/13% DMSO/15% tea tree oil/69% isopropyl alcohol to persons diagnosed with plantar fasciitis resulted in a dramatic improvement in reported patient pain scores in 89% of those treated in the active group. Application of Composition A (tea tree oil with DMSO) or Composition B (clove oil with DMSO) resulted in some improvement in pain scores but did not reach significance. However, the combination of clove oil with tea tree oil (Composition C) when administered with DMSO had a marked and dramatic synergistic effect on reducing pain scores in participants with plantar fasciitis. While tea tree oil and clove oil are both known to possess anti-inflammatory activity, the pronounced synergistic effect seen with the combination is unexpected, surprising, novel, and not something that a person skilled in the art would have been able to predict.

FIG. 1 is an exemplary flow chart of embodiments of treating plantar fasciitis in accordance with the disclosure. As shown, method 100 may begin with step 102 of optionally cleaning and drying the area to be treated (e.g., the heel of the foot), if it has not already been cleaned. Then at 104 the composition is applied to the area to be treated. As disclosed herein, Composition C above has proven effective in treatment. Further, the composition may be applied in accordance with the form of the composition. For example, for liquid compositions, application may be with a brush or sponge, while cream-like compositions may be applied by hand.

As indicated at 106, and disclosed herein, twice daily application of the composition has been shown effective, thus, time is allowed to lapse before performing a second application as indicated at 108 and 110. Method 100 may be repeated for a period of 3 to 20 days as desired.

Although various embodiments have been shown and described, the present disclosure is not so limited and will be understood to include all such modifications and variations are would be apparent to one skilled in the art.

What is claimed is:

1. A topical composition for treating a symptom of plantar fasciitis, the composition comprising in effective amounts therefor:
   (i) essential oil of tea tree oil;
   (ii) essential oil of clove bud oil;
   (iii) a skin permeation agent selected from the group consisting of dimethylsulfoxide (DMSO), dimethylsulphacetamide, terpenes, long chain alcohols, pyrrolidones, and cinnamene compounds; and
   (iv) an alcohol carrier and/or an inert carrier oil.

2. The composition of claim 1, wherein the tea tree is *Melaleuca alternifolia* and/or the clove is *Syzygium aromaticum*.

3. The composition of claim 1, wherein:
the alcohol carrier selected from the group consisting of methanol, ethanol, 1-propanol, isopropyl alcohol, butanol, isobutyl alcohol, pentanol, tert-amyl alcohol, hexanol, cyclohexanol, benzyl alcohol, and cetyl alcohol; and/or
the inert carrier oil is selected from the group consisting of almond oil and canola oil.

4. The composition of claim 1, wherein by percent volume of the composition:
the tea tree oil is present in an amount of from 1% (v/v) to 50% (v/v);
the essential oil of clove bud oil is present in an amount of from 1% (v/v) to 50% (v/v);
the carrier alcohol and/or inert carrier oil is present in an amount of from 10% (v/v) to 80%, (v/v); and
the skin permeation agent in an amount of from 1% (v/v) to 25% (v/v).

5. The composition of claim 1, wherein by percent volume of the composition:
the tea tree oil is present in an amount of from 7% (v/v) to 20% (v/v);
the essential oil of clove bud oil is present in an amount of from 1% (v/v) to 5% (v/v);
the carrier alcohol and/or inert carrier oil is present in an amount of from 60% (v/v) to 80% (v/v); and
the skin permeation agent in an amount of from 5% (v/v) to 20% (v/v).

6. The composition of claim 1, wherein the skin permeation agent comprises DMSO or dimethylsulphacetamide and wherein composition comprises, by percent volume of the composition: 15% (v/v) tea tree oil, 3% (v/v) essential oil of clove bud oil, 13% (v/v) DMSO or dimethylsulphacetamide, and 69% (v/v) alcohol carrier or inert carrier oil.

7. The composition of claim 1, wherein said terpene is limonene or a mixture of terpenes, and/or said long chain alcohol is 1-octanol.

8. A method of treating an inflammatory condition in a human subject, the method comprising administering to the skin of the human subject in the area of the inflammatory condition a composition comprising, in therapeutically effective amounts therefor:
(i) essential oil of tea tree oil;
(ii) essential oil of clove bud oil;
(iii) a skin permeation agent selected from the group consisting of dimethylsulfoxide (DMSO), dimethylsulphacetamide, terpenes, long chain alcohols, pyrrolidones, and cinnamene compounds; and
(iv) an alcohol carrier and/or an inert carrier oil,
wherein the inflammatory condition is plantar fasciitis.

9. The method of claim 8, wherein the tea tree is *Melaleuca alternifolia* and/or the clove is *Syzygium aromaticum*.

10. The method of claim 8, wherein:
the alcohol carrier selected from the group consisting of methanol, ethanol, 1-propanol, isopropyl alcohol, butanol, isobutyl alcohol, pentanol, tert-amyl alcohol, hexanol, cyclohexanol, benzyl alcohol, and cetyl alcohol; and/or
the inert carrier oil is selected from the group consisting of almond oil and canola oil.

11. The method of claim 8, wherein the administered composition comprises, by percent volume of the composition:
tea tree oil in an amount of from 1% (v/v) to 50% (v/v);
essential oil of clove bud in an amount of from 1% (v/v) to 50% (v/v);
carrier alcohol and/or inert carrier oil in an amount of from 10% (v/v) to 80%, (v/v); and
skin permeation agent in an amount of from 1% (v/v) to 25% (v/v).

12. The method of claim 8, wherein the administered composition comprises, by percent volume of the composition:
tea tree oil in an amount of from 7% (v/v) to 20% (v/v);
essential oil of clove bud oil in an amount of from 1% (v/v) to 5% (v/v);
carrier alcohol and/or inert carrier oil in an amount of from 60% (v/v) to 80% (v/v); and
skin permeation agent in an amount of from 5% (v/v) to 20% (v/v).

13. The method of claim 8, wherein the skin permeation agent comprises DMSO or dimethylsulphacetamide and wherein the administered composition comprises, by percent volume of the composition: 15% (v/v) tea tree oil, 3% (v/v) essential oil of clove bud oil, 13% (v/v) DMSO or dimethylsulphacetamide, and 69% (v/v) alcohol carrier or inert carrier oil.

14. The method of claim 8, wherein said terpene is limonene or a mixture of terpenes, and/or said long chain alcohol is 1-octanol.

15. The method of claim 8, wherein the administering the composition comprises administering twice a day.

16. The method of claim 8, wherein the administering the composition comprises administering for a period of 3 to 20 days.

17. A method of making a composition usable for treatment of an inflammatory condition in human subjects wherein the inflammatory condition is plantar fasciitis, the method comprising mixing, in effective amounts therefor: (i) essential oil of tea tree oil; (ii) essential oil of clove bud oil; (iii) a skin permeation agent selected from the group consisting of dimethylsulfoxide (DMSO), dimethylsulphacetamide, terpenes, long chain alcohols, pyrrolidones, and cinnamene compounds; and (iv) an alcohol carrier and/or an inert carrier oil.

18. The method of claim 17, wherein the tea tree is *Melaleuca alternifolia* and/or the clove is *Syzygium aromaticum*.

19. The method of claim 17, wherein:
the alcohol carrier selected from the group consisting of methanol, ethanol, 1-propanol, isopropyl alcohol, butanol, isobutyl alcohol, pentanol, tert-amyl alcohol, hexanol, cyclohexanol, benzyl alcohol, and cetyl alcohol; and/or
the inert carrier oil is selected from the group consisting of almond oil and canola oil.

20. The method of claim 17, wherein the administered composition comprises, by percent volume of the composition:
tea tree oil in an amount of from 1% (v/v) to 50% (v/v);
essential oil of clove bud in an amount of from 1% (v/v) to 50% (v/v);
carrier alcohol and/or inert carrier oil in an amount of from 10% (v/v) to 80%, (v/v); and
skin permeation agent in an amount of from 1% (v/v) to 25% (v/v).

21. The method of claim 17, wherein the administered composition comprises, by percent volume of the composition:
tea tree oil in an amount of from 7% (v/v) to 20% (v/v);
essential oil of clove bud oil in an amount of from 1% (v/v) to 5% (v/v);

carrier alcohol and/or inert carrier oil in an amount of from 60% (v/v) to 80% (v/v); and skin permeation agent in an amount of from 5% (v/v) to 20% (v/v).

22. The method of claim 17, wherein the skin permeation agent comprises DMSO or dimethylsulphacetamide and wherein the administered composition comprises, by percent volume of the composition: 15% (v/v) tea tree oil, 3% (v/v) essential oil of clove bud oil, 13% (v/v) DMSO or dimethylsulphacetamide, and 69% (v/v) alcohol carrier or inert carrier oil.

23. The method of claim 17, wherein said terpene is limonene or a mixture of terpenes, and/or said long chain alcohol is 1-octanol.

* * * * *